United States Patent
Faghri et al.

(10) Patent No.: US 9,687,846 B2
(45) Date of Patent: Jun. 27, 2017

(54) ENHANCED MICROFLUIDIC VALVES FOR MEDIA DIAGNOSTICS

(71) Applicant: Board of Governors for Higher Education, State of Rhode Island and Providence Plantations, Providence, RI (US)

(72) Inventors: Mohammad Faghri, East Greenwich, RI (US); Constantine Anagnostopoulos, North Kingstown, RI (US); Hong Chen, South Kingstown, RI (US); Jeremy Cogswell, Johnston, RI (US)

(73) Assignee: Council on Postsecondary Education, Warwick, RI (US)

( * ) Notice: Subject to any disclaimer, the term of this patent is extended or adjusted under 35 U.S.C. 154(b) by 20 days.

(21) Appl. No.: 14/216,503

(22) Filed: Mar. 17, 2014

(65) Prior Publication Data
US 2014/0295533 A1    Oct. 2, 2014

Related U.S. Application Data

(60) Provisional application No. 61/791,457, filed on Mar. 15, 2013.

(51) Int. Cl.
*B01L 3/00* (2006.01)
*B01L 1/00* (2006.01)
*G01N 33/543* (2006.01)

(52) U.S. Cl.
CPC ....... *B01L 3/502738* (2013.01); *B01L 3/5023* (2013.01); *G01N 33/54366* (2013.01);
(Continued)

(58) Field of Classification Search
CPC ............ B01L 3/502738; B01L 3/5023; B01L 2200/0621; B01L 2300/0874; B01L 2300/0887; B01L 2400/0406; B01L 2400/0688; B01L 2400/06; B01L 2300/126; G01N 33/54366
(Continued)

(56) References Cited

U.S. PATENT DOCUMENTS 6,068,751 A    5/2000   Neukermans
6,167,910 B1   1/2001   Chow
(Continued)

FOREIGN PATENT DOCUMENTS

JP         2004317498 A    11/2004

OTHER PUBLICATIONS

International Search Report and Written Opinion mailed on Aug. 20, 2014 in connection with International Application PCT/US2014/030566, 14 pages.

*Primary Examiner* — Nathan Bowers
(74) *Attorney, Agent, or Firm* — Gesmer Updegrove LLP

(57) ABSTRACT

The invention provides a micro-fluidic device that includes a pre-loaded sample that begins to flow only when a sample is provided in the device. In certain embodiments, the invention provides a micro-fluidic device including at least two paper flow path layers providing fluid flow in substantially parallel planar directions, and at least one valve positioned between the at least two paper flow paths, wherein the at least one valve for providing flow in a direction that is orthogonal to the substantially planar directions.

9 Claims, 18 Drawing Sheets

(52) U.S. Cl.
CPC ............... *B01L 2200/0621* (2013.01); *B01L 2300/0874* (2013.01); *B01L 2300/0887* (2013.01); *B01L 2300/126* (2013.01); *B01L 2400/0406* (2013.01); *B01L 2400/0688* (2013.01)

(58) Field of Classification Search
USPC ..................................................... 435/287.2
See application file for complete search history.

(56) References Cited

U.S. PATENT DOCUMENTS

| | | |
|---|---|---|
| 2004/0053403 A1 | 3/2004 | Jedrzejewski et al. |
| 2011/0030809 A1 | 2/2011 | Ying et al. |
| 2011/0123398 A1* | 5/2011 | Carrilho ............ B01L 3/502738 422/68.1 |
| 2013/0078711 A1 | 3/2013 | Chen et al. |

* cited by examiner

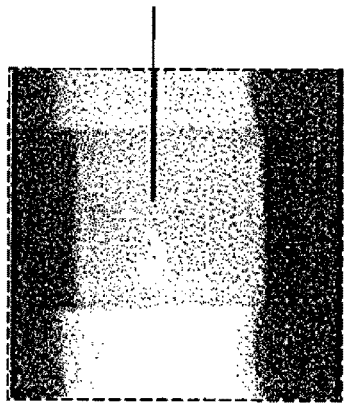
Negative control: No Rabbit IgG Present in the Sample Fluid, No Signal is Visible
FIG. 5B
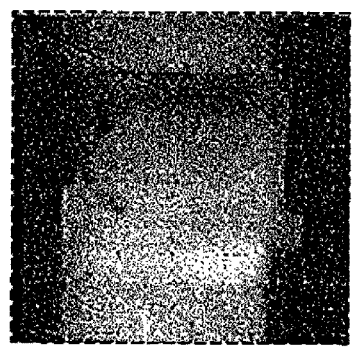
10 ng/mL Concentration of Rabbit IgG in the Sample
FIG. 5C
B. Results
Conjugate Pad
FIG. 5B
FIG. 5C
FIG. 5A

1. immobilization 2. blocking 3. inhibition 4. enzymatic reaction 5. stop of reaction

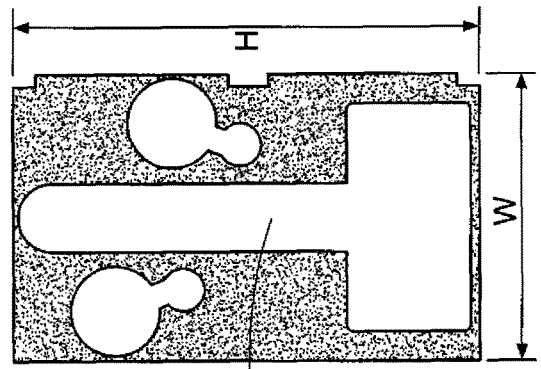
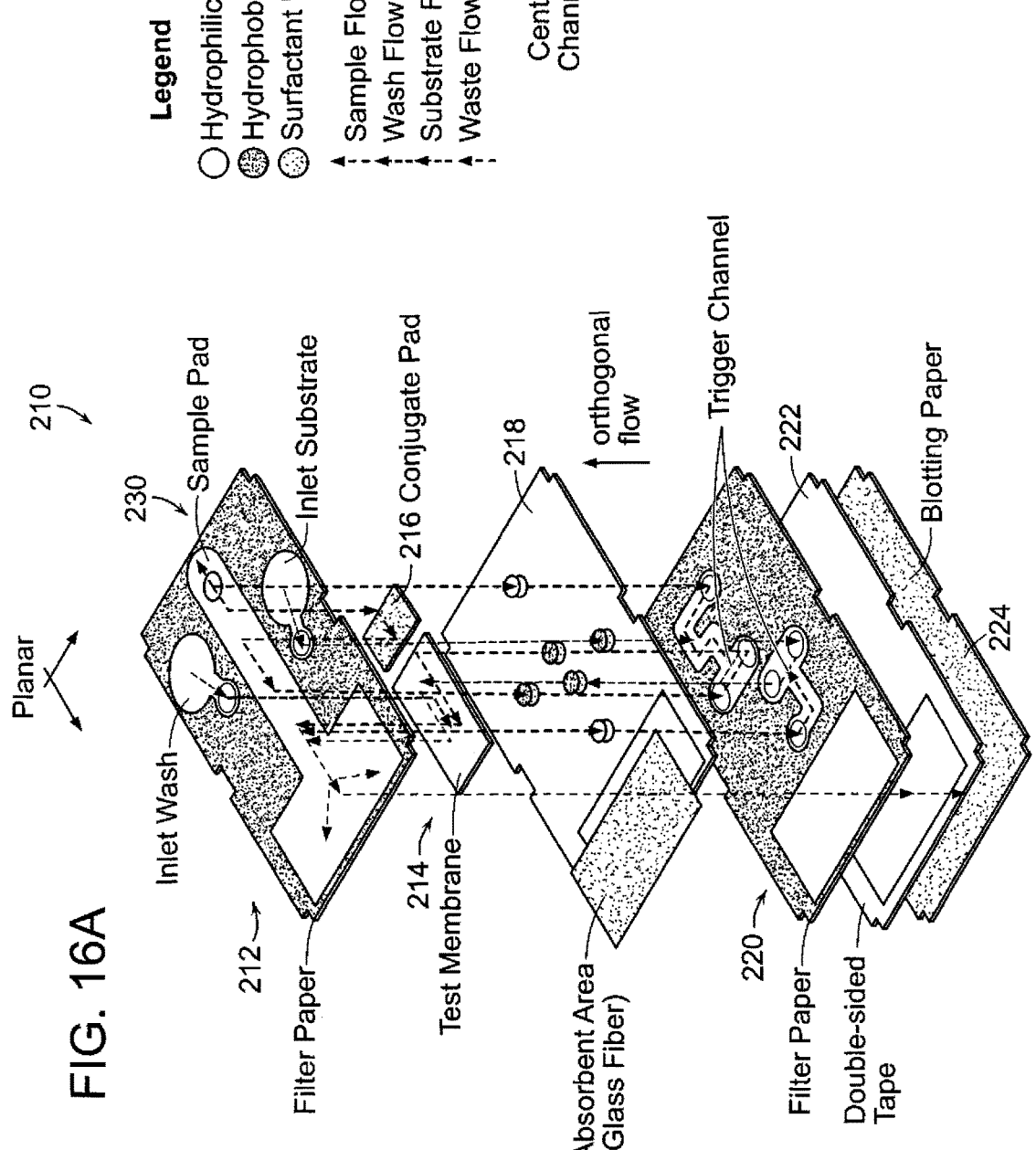
FIG. 16A
FIG. 16B

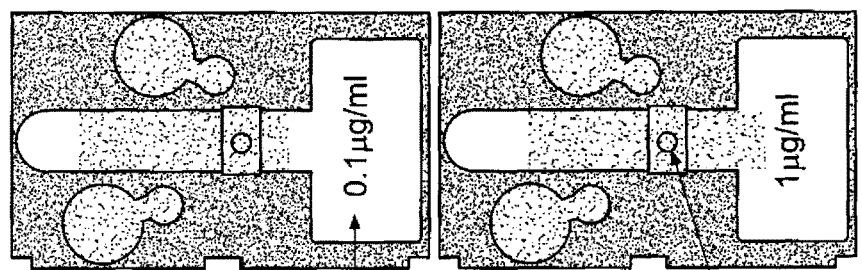
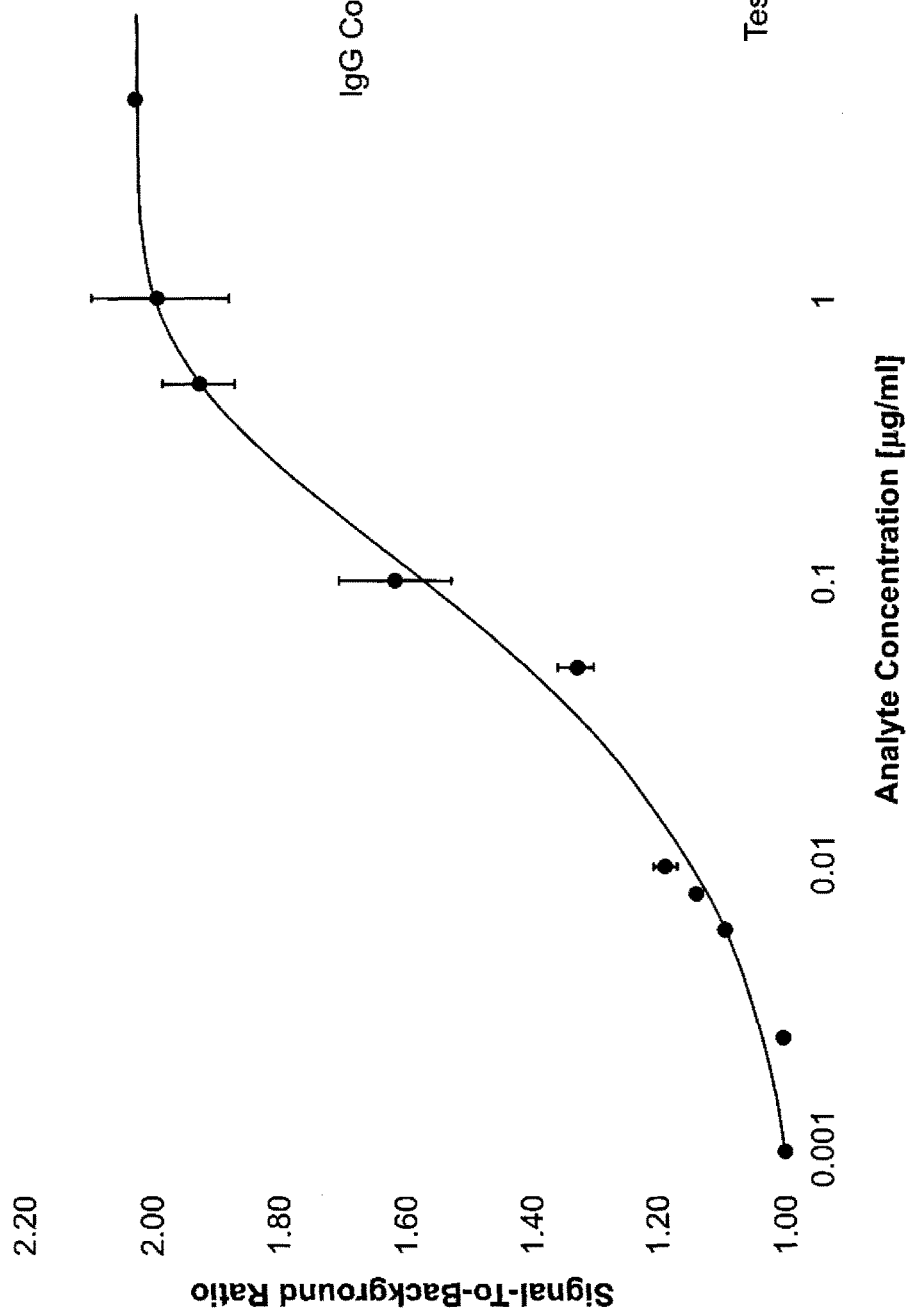
FIG. 18B
FIG. 18A

ENHANCED MICROFLUIDIC VALVES FOR MEDIA DIAGNOSTICS

PRIORITY

The present application claims priority to U.S. Provisional Patent Application Ser. No. 61/791,457 filed Mar. 15, 2013, the disclosure of which is hereby incorporated by reference in its entirety.

BACKGROUND

Considerable effort has been expanded over the last couple of decades to develop point-of-care diagnostic tests. The glucose meter is one such successful product used by millions daily around the world to monitor the sugar level in their blood. A second is the home pregnancy test kit. Both devices are low cost, easy to use, highly accurate and reliable.

The pregnancy test kits utilize Lateral Flow Immunochromatographic Assay Devices more commonly referred to as Lateral Flow Test Strips or simply Test Strips. Such test strips are available in the market also for detecting other proteins or molecules in biological fluids. However, their success as products is limited for a number of reasons, such as that their signal fades with time, their sensitivity it too low or because they are not simple enough to use.

The gold standard for the detection of proteins is ELISA (Enzyme Linked Immunosorbent Assay) which requires a number of reagents to be applied sequentially to the detection site. Test strips cannot perform ELISA because they are limited to only one fluid, typically the sample fluid, which precludes an enzymatic reaction that requires, at the very least, the introduction of a substrate. Test strips incorporating more fluids have been commercialized but these devices are no longer simple to use.

U.S. Patent Application Publication No. 2013/0078711 discloses the use of a paper based microfluidic valve (PBMV) for achieving these goals by being able to perform ELISA on modified Lateral Flow Test Strips.

What is needed to make test strips broadly commercially successful is to be able to modify them so that more fluids are used for the assay but those reagents flow autonomously and entirely transparently to the user, thus maintaining the strip test's simplicity of use, while producing more valuable results. There remains a need therefore, for microfluidic devices that meet these needs.

SUMMARY

In accordance with an embodiment, the invention provides a micro-fluidic device that includes a pre-loaded sample that begins to flow only when a sample is provided in the device.

In accordance with another embodiment, the invention provides a micro-fluidic device comprising at least two paper flow path layers providing fluid flow in substantially parallel planar directions, and at least one valve positioned between the at least two paper flow paths, wherein the at least one valve for providing flow in a direction that is orthogonal to the substantially planar directions.

In accordance with a further embodiment, the invention provides a method providing a micro-fluidic device, wherein the method includes the steps of providing paper flow path layers on either side of a hydrophobic material, wherein the hydrophobic material includes actuatable valves between the paper flow path layers.

BRIEF DESCRIPTION OF THE DRAWINGS

The following description may be further understood with reference to the accompanying drawings in which:

FIG. 5 shows an illustrative diagrammatic illustration of a device of the invention showing visible results of a test;

FIG. 16A shows an illustrative diagrammatic exploded view of a three-fluid device in accordance with an embodiment of the invention, and FIG. 16B shows an illustrative diagrammatic top view of the device of FIG. 16A;

FIG. 18A shows an illustrative graphical representation of a dose response curve for a device in accordance with an embodiment of the invention, and FIG. 18B shows a pair of actual devices following a test.

The drawings are shown for illustrative purposes only.

DETAILED DESCRIPTION

The invention provides an enhanced paper based microfluidic valve that is capable of conducting ELISA (EnzymeLinked Immuno-Sorbent Assay) on porous media substrates. The invention allows for sequential manipulation of multiple fluids without operator intervention. Specifically it can, for example, incorporate washing and signal amplification, in a single assay to lower background signal level, eliminate signal fading and enhance sensitivity.

Paper based microfluidic valve technology (PBMV) is capable of conducting ELISA (Enzyme-Linked Immuno-Sorbent Assay) on porous media substrates such as paper. PBMV allows for sequential manipulation of multiple fluids without operator intervention. Specifically it can, for example, incorporate washing and signal amplification, in a single assay to lower background signal level, eliminate signal fading and enhance sensitivity. The technology constitutes a new platform for disposable, very low cost diagnostic devices.

The core of the PBMV technology is the fluidic valve or diode that can be formed in a variety of porous media. It is a two terminal device that allows wicking of a fluid if it enters from the valve's forward direction but stops the wicking if the fluid enters from the reverse direction. Using this basic element, fluidic circuits, such as triggers and delays can be printed on paper, which, when connected in specific arrangements, can control the flow of two or more fluids at once, similar to what electrical circuits do for the flow of current.

Figure 1:
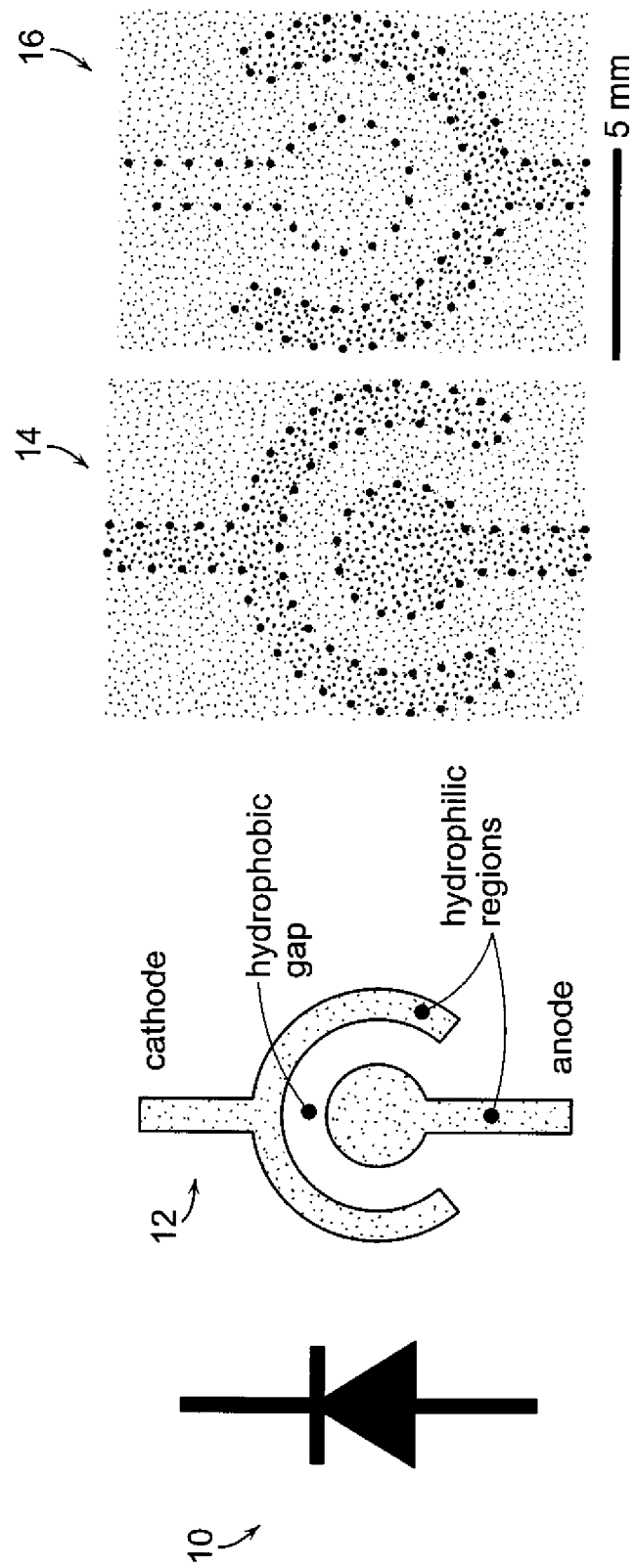
FIGS. 1A-1D show illustrative schematic representations of devices in accordance with an embodiment of the invention.

A symbol of the valve is shown at 10 in FIG. 1 A and its actual layout is shown at 12 in FIG. 1B. FIG. 1B, is a top view of the two-terminal fluidic valve fabricated on paper. The device consists of a group of hydrophilic regions separated by a hydrophobic gap. All other regions of the paper are also hydrophobic. The hydrophobic regions are formed by soaking the s paper in a solution containing Allyltrichlorosilane. This process coats the cellulose fibers with a vinyl group thereby creating a virtual hydrophobic wall while maintaining the structural porosity of the paper. A small amount of TWEEN 20 surfactant is deposited and dried at the circular section of the valve's inlet.

In FIG. 1C it is shown at 14 that if a fluid (water containing green food coloring) is introduced at the valve's inlet or anode, then the fluid easily bridges the hydrophobic gap and continues on to the valve's outlet or cathode. However, if the fluid is introduced at the valve's cathode, as it is done in FIG. 1D (shown at 16), the fluid is stopped by the hydrophobic gap. One important feature of the fluidic valve is that once fluid has penetrated the hydrophobic gap, it is then open to fluid flow in both directions.

Figure 2:
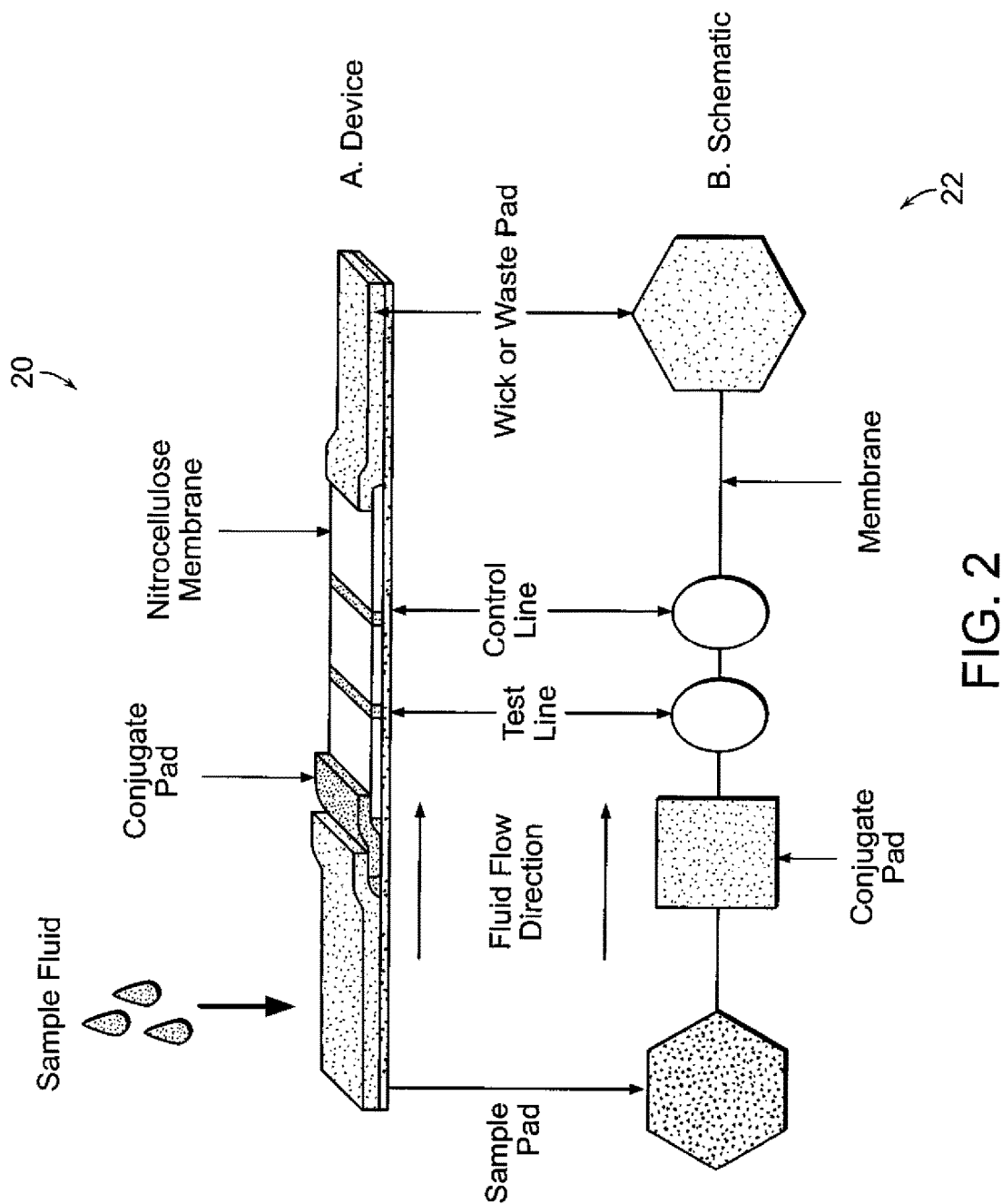
FIG. 2 shows an illustrative diagrammatic representation of a system employing a device in accordance with embodiment of the invention.
Figure 3:
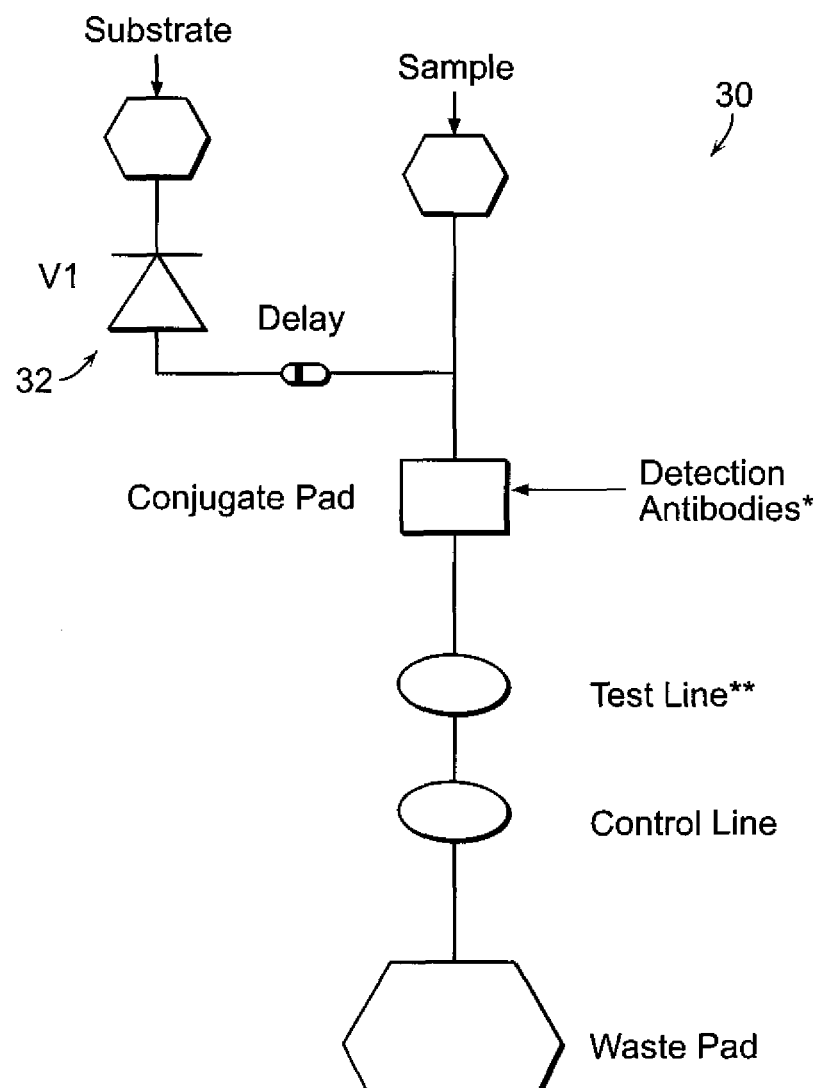
FIG. 3 shows an illustrative schematic representation of a device in accordance with another embodiment of the present invention.

Combining the conventional lateral flow test strip (LFT) technology with our paperbased microfluidic valve (PBMV) technology, we are able to create a number of new LFT devices. In FIG. 2 a conventional LFT device is shown at 20 and below it a schematic representation of the device is shown at 22. A schematic of one new LFT device incorporating one fluidic diode is shown at 30 in FIG. 3.

Figure 4:
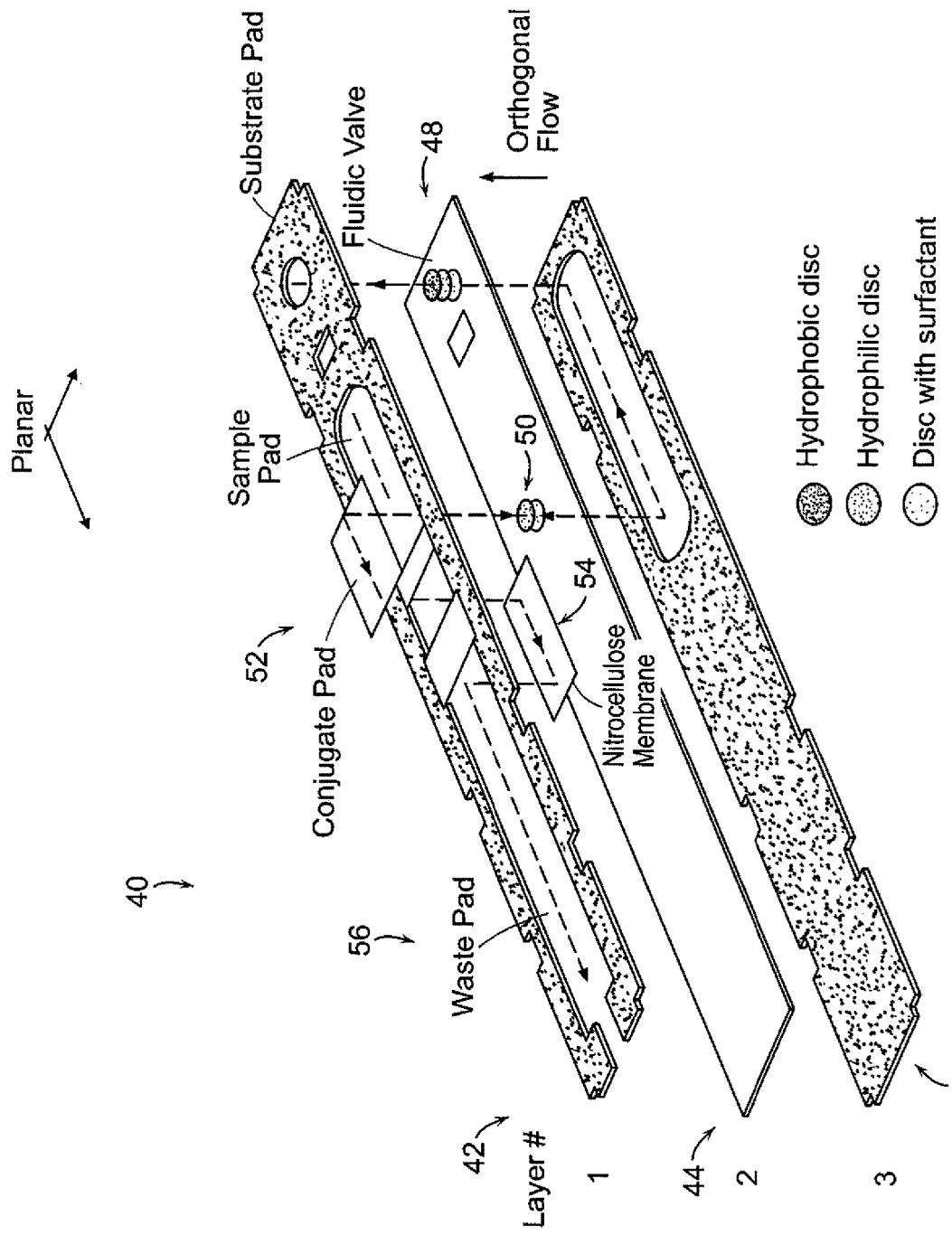
FIG. 4 shows an illustrative diagrammatic representation of a device in accordance with a further embodiment of the invention.

This device is capable of conducting ELISA. This is possible because now a second fluid, beside the sample, a substrate, can be preloaded onto the device and it begins to flow only after the sample is loaded onto the sample pad. To see how the device works, consider FIG. 4. In FIG. 4 is shown the actual device layout at 40. It consists of three layers 42, 44, 46. The top and bottom layers are held together by the middle layer which is a double sided tape. The top layer, 42, consists of filter paper onto which a pattern of black wax is printed. This wax is melted and driven into the paper plugging the pores and forming solid hydrophobic walls. The white regions are virgin paper and are hydrophilic. Three cuts are made on this layer. One cut is bridged by a nitrocellulose membrane. This is where the test line is located and is defined by a line of immobilized capture antibodies. The other cut is bridged by a fiberglass membrane in which there have been dried the detection antibodies each tagged with and enzyme. The third cut near the top is for venting and as an observation window.

The middle layer 44 is a double sided tape. It has two round holes punched in it. The hole in the middle is filled with a disc of virgin paper. The hole near the top is filled with two discs. The bottom one consists of paper infused with Tween-20 surfactant. The disc on top of it is made of paper but made hydrophobic by treating it with Allyltrichlorosilane. Unlike the hydrophobic regions made with wax, in which the pores are plugged, in this disc the pores are still present and open. This is the valve, designated as V1 and shown at 32 in FIG. 3 and at 48 in FIG. 4. It behaves the same way as the fluidic valve described in FIG. 1, but it is made in 3-D.

In operation, the substrate solution is preloaded onto the substrate pad or placed there at the same time as the sample is loaded onto the sample pad. The substrate cannot flow past the valve because it is entering it from the reverse direction. The sample fluid does begin to flow. Just before it reaches the conjugate pad it splits into two streams, shown by the dashed line in FIG. 4. One stream goes through the conjugate pad 52, where it picks up the detection antibodies which conjugate with the antigens in the sample solution, and continues on to the nitrocellulose membrane 54, where the conjugate is captured by the immobilized capture antibodies, and the remaining fluid continues on to the waste pad 56. The other stream goes through the middle hole in layer #2 shown at 50 and into the fluidic channel in layer #3 below where it flows towards the valve 48. Since it approaches the valve from its forward direction the valve opens and triggers the substrate solution to begin flowing. The substrate now flows towards the middle hole in layer #2 and up to layer #1, then through the conjugate pad and into the nitrocellulose membrane 54 where it interacts with the captured enzymes forming a colored product that deposits on the test line and continues flowing down to the waste pad 56 until the supply of substrate is exhausted. FIG. 5B shows comparative results of an enzymatic reaction, demonstrating a limit of detection of about 10 ng/mL for Rabbit IgG. More recent results have shown a limit of detection of 0.1 pg/mL.

Figure 6:
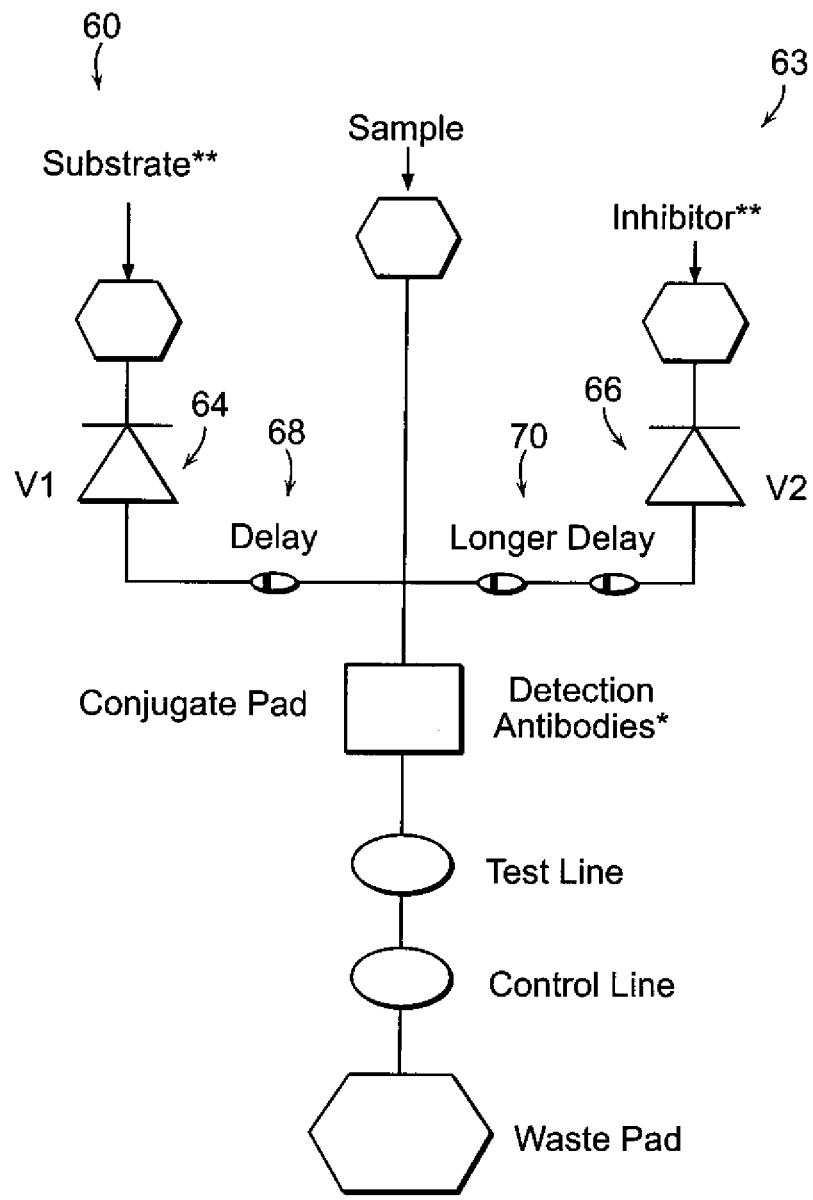
FIG. 6 shows illustrative diagrammatic representation of a device in accordance with a further embodiment of the invention.
Figure 7:
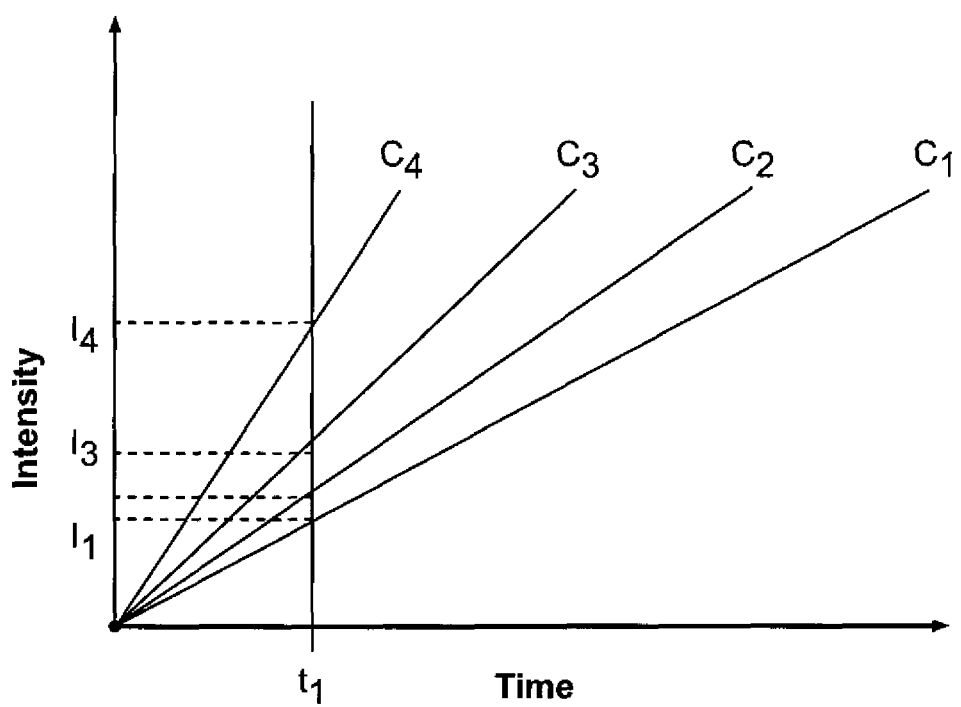
FIG. 7 shows an illustrative diagrammatic graphical representation of plot of signal intensity as function of time for various IαIP concentrations, where C4<C3<C2<C1. TQ is the time from when the sample was applied till the stop solution is triggered and subsequently quenches the enzymatic activity.

It is sometimes desirable to have quantitative data from an assay, such as to know the concentration of the analyte in the sample, rather than whether the analyte is present or not in the solution at some level above the detection limit. This can be accomplished with an enzymatic reaction, as has been described here but adding an inhibitor to the process to stop the reaction at some predetermined time after the start of the assay. To accomplish this, two extra fluids must now flow past the test line in sequence, besides the sample fluid, of course. A device to do that is shown in FIG. 6A and the expected results in FIG. 6B. As may be seen in FIG. 6A, the device includes two flow paths 60, 62, and each has a valve 64, 66. The substrate path 60 may include a delay device 68, and the inhibitor path may include a longer delay device 70. Antibodies are labeled with an enzyme for true ELISA and higher sensitivity, no signal fading and quantitative results. Substrate and inhibitor solutions are preloaded onto the pads and triggered to flow by the sample fluid. FIG. 7 shows the dependence of intensity on time for various analytre concentrations, C1-C4.

While there is no theoretical limit as to how many fluids may be loaded into one device, each of which will require at least on valve, Also, there is also no theoretical limit as to what fluids, besides the sample, may be included.

Figure 8:
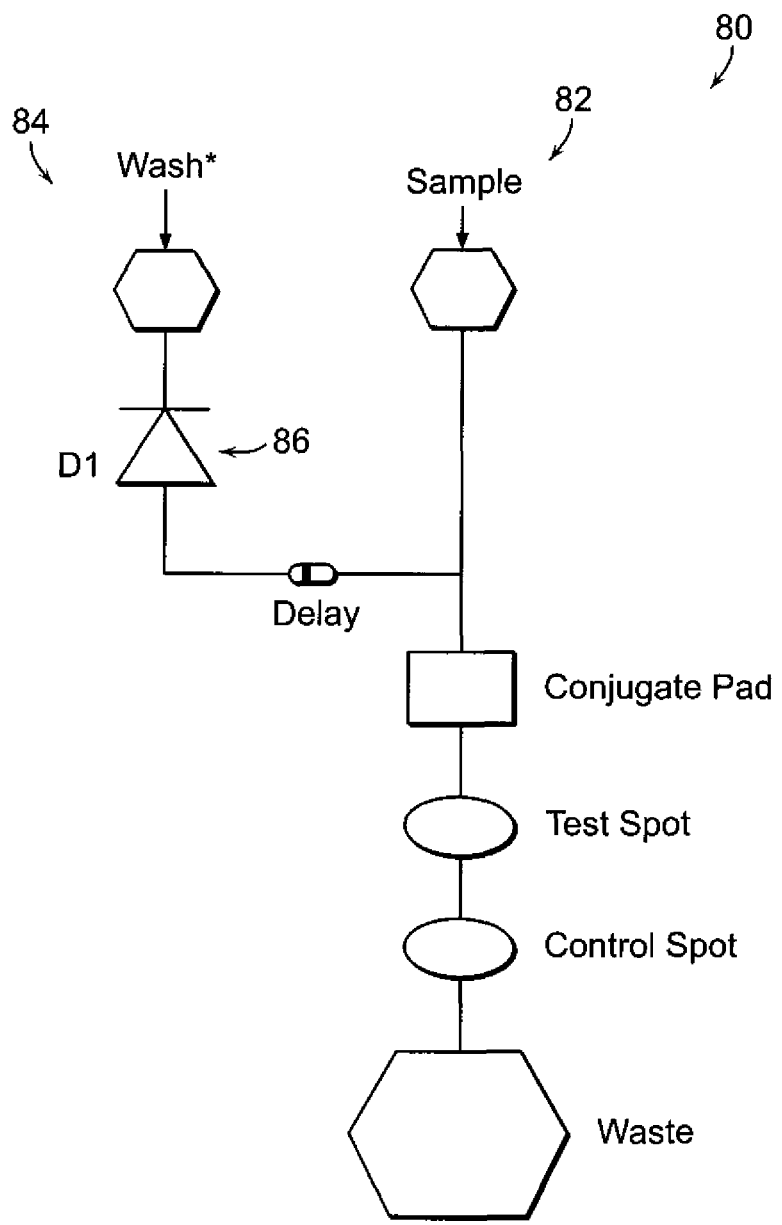
FIG. 8 shows an illustrative schematic view of device in accordance with another embodiment of the invention that includes a wash flow path.

In FIG. 8, for example, it is shown that a wash may be added as a second fluid to a device that is conducting a typical LFT assay where the detection antibodies are tagged with gold nanoparticles. The system 80 includes a sample path 82 and a wash path 84 having a valve 86. Here a wash may be provided to reduce the background signal. In another case a silver enhancer solution can be used to amplify the signal. Experimental studies to demonstrate the quantitative assay described in FIG. 6 and other assays mentioned with respect to FIG. 8 are currently under way as well as studies focusing on the detection of disease biomarkers of clinical interest.

The invention therefore, provides for conducting, autonomously, a quantitative enzymatic assay to determine the concentration of Inter alpha Inhibitor Protein (IαIP) in buffer, which is a biomarker for sepsis. While in healthy adult individuals, the amount of circulating IαIP in blood is relatively high (between 300-600 mg/L), IαIP levels decrease rapidly during systemic inflammation and sepsis. In severe cases, IαIP may be depleted up to 90% of the baseline value. As the disease progress to more advanced and life-threatening levels, IαIP levels drop precipitously, suggesting IαIP's clinical utility as a prognostic marker in assisting clinicians in monitoring disease progression and making informed treatment decisions. The development of a rapid point-of-care IαIP test that can be used to identify life-threatening conditions with a simple, user-friendly and portable device is therefore desirable. Moreover, replacement therapy with highly purified IαIP isolated from human plasma has been shown to be beneficial in reducing mortality in experimental animals challenged with deadly bioterrorism agents such as anthrax toxin.

Figure 9:
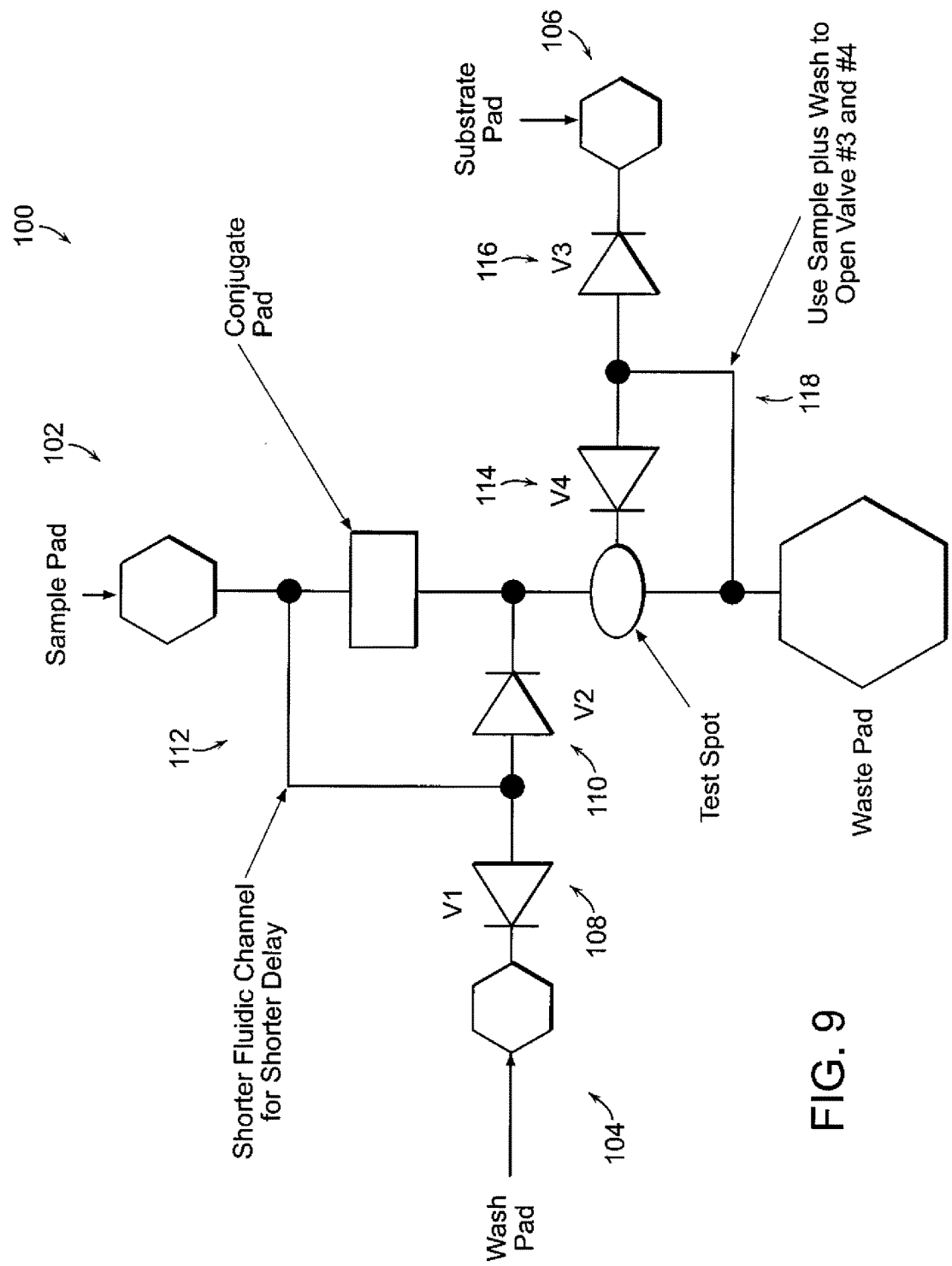
FIG. 9 shows an illustrative schematic view of a device in accordance with a further embodiment of the invention that includes a wash flow path as well as variable delay functionality.

FIG. 9, for example, shows a device 100 in accordance with a further embodiment of the present invention that includes a sample pad path 102, a wash pad path 104, and a substrate pad path 106. The wash pad path includes two opposing valves 108, 110 with a fluidic channel 112 between them coupled to the sample pad path. The substrate pad path also includes two opposing valves 114, 116 with a fluidic channel 118 coupled to the path to the waste pad.

Figure 10A:
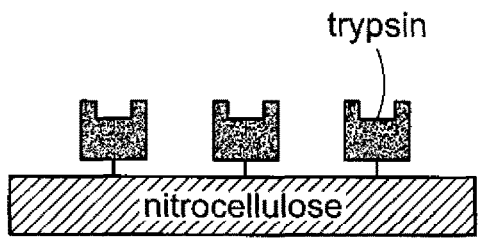
FIGS. 10A-10E show illustrative schematic views of the enzymatic assay at the test spot as a function of time for a lab-on-paper device for the detection of Inter-alpha inhibitor proteins.
Figure 10B:
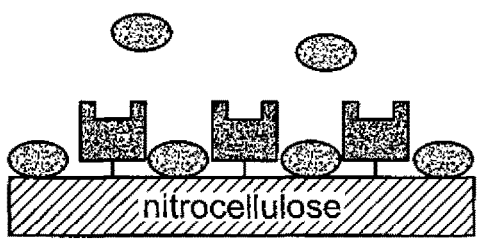

Inter-alpha Inhibitor Proteins function by deactivating enzymes such as trypsin. A schematic of the assay, we will be conducting on our Lab-on-paper devices, at the test point is shown schematically in FIGS. 10A-10E. In FIG. 10A it is shown that a certain concentration of trypsin enzymes are immobilized at a surface, which in our case would be the surfaces of fibers contained in the test spot in the nitrocellulose membrane. This is done during device fabrication. Also during device fabrication a blocking step using BSA, shown in FIG. 10B, is performed to make sure the IαI proteins do not get captured by the nitrocellulose membrane. Prior to conducting the test, the substrate and stop solutions are loaded in their respective pads shown in FIG. 11. The valves below those pads prevent them from flowing.

Figure 10C:
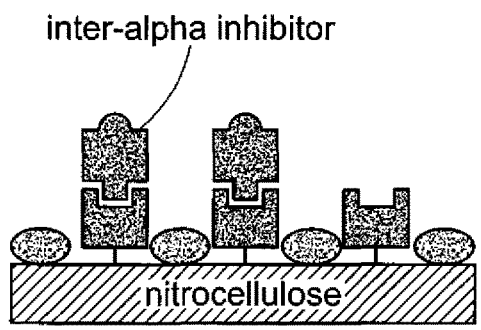

At the time of the test, a sample containing IαIP is loaded onto the input pad and begins to flow through the test spot, FIG. 10C. A number of the enzymes are then deactivated by these proteins. In addition, a portion of the sample solution flows through a separate path, not visible in FIG. 11, to the paper layer below and after some time it reaches the valves and turns them on. At this time the substrate solution begins to flow toward the test spot.

Figure 10D:
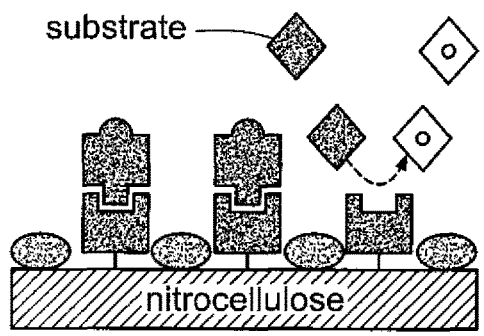
Figure 10E:
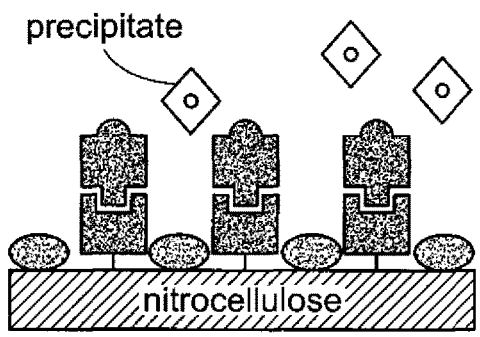

As shown in FIG. 10D, the chromogenic substrate (BAPNA) reacts with the enzymes that have remained active to produce a colored product that precipitates around the test spot. This will be the signal that is eventually read out. After an additional time has elapsed, the valves beneath the stop solution are turned on by a portion of the fluid that has passed through the test spot. This now allows the stop solution, such as BPTI (Basic Pancreatic Trypsin Inhibitor), to flow to the test spot and deactivate the remaining enzymes and quench the generation of the product. This is shown schematically in FIGS. 10E.

FIGS. 10A-10E therefore, show schematic diagrams of the enzymatic assay at the test spot as a function of time for a lab-on-paper device for the detection of the Inter-alpha inhibitor proteins.

Figure 11:
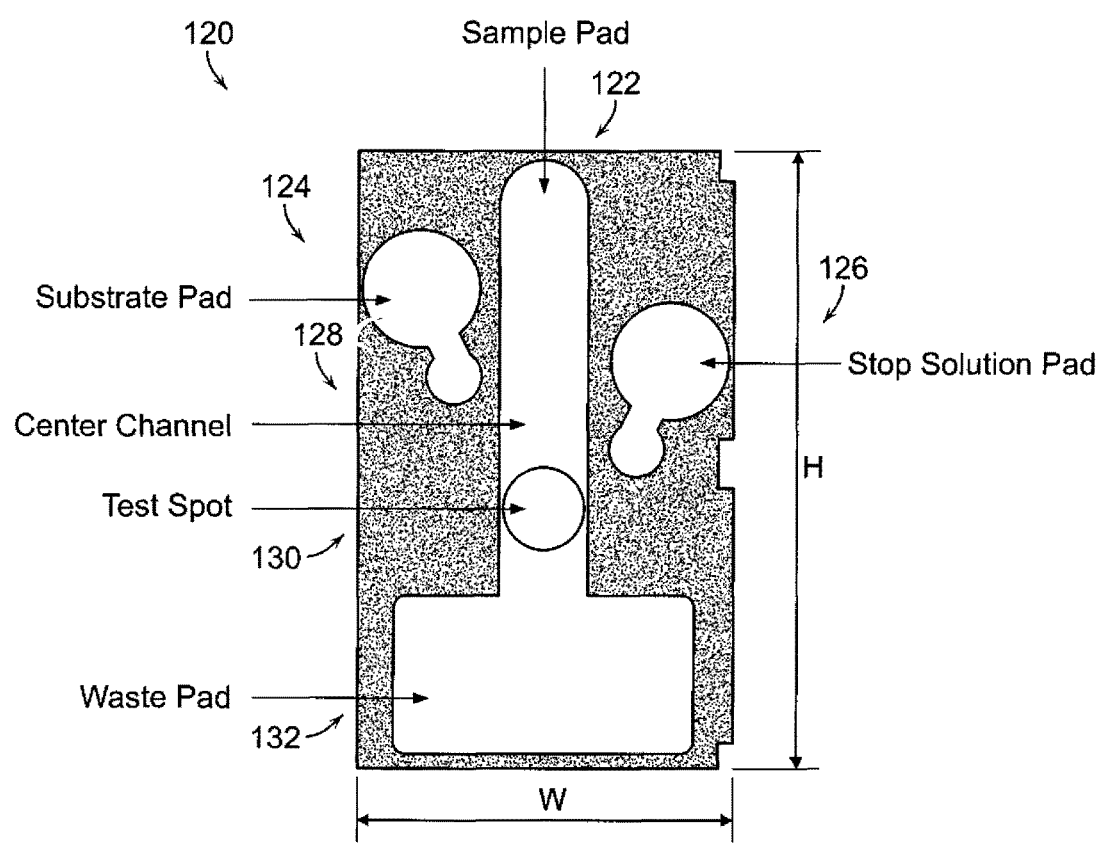
FIG. 11 shows an illustrative top view of a device in accordance with an embodiment of the present invention.

To conduct the above assay a device may be provided that can handle three different reagents, the sample, the substrate and the enzymatic activity stop solution, as for example shown in FIGS. 16A and 16B below. FIG. 11 shows a top view of the device, having a width of about 23 mm and a height of about 36 mm and a thickness of about 2 mm. The device 120 includes a sample pad 122, a substrate pad 124, a stop solution pad 126, a center channel 128 with a test spot 130 and a waste pad 132

An enzymatic activity may produce a linear signal as function of time. FIG. 7 above shows this schematically. In FIG. 7 the signal level, which may be the darkness of the test spot, increases with time as long as the substrate keeps flowing past it and saturation is not yet reached. As seen in the FIG. 7, the rate of signal darkness or intensity is lower for higher concentrations of IαIP in the sample, because more enzymes have been deactivated by them. $T_Q$ corresponds to the time spanned between when the sample was applied and when the stop solution was released and quenched the activity at the test spot.

From experiments, a plot may be made of test spot darkness, measured using ImageJ, vs IαIp concentration in the sample for a given $T_Q$. This curve will then serve as the calibration for our system. It will be used to determine the unknown concentration of IαIp in a sample.

Eventually, the concentration of IαIP in plasma will need to be determined. In the plasma are a number of other inhibitors, besides IαIP, which can deactivate the trypsin enzymes. To address this problem a dual device may be used as shown at 140 in FIG. 12. The dual device 140 includes two devices 142, 144 similar to device 120 of FIG. 11, wherein ach of the devices is commonly coupled to a common sample pad 146.

Figure 12:
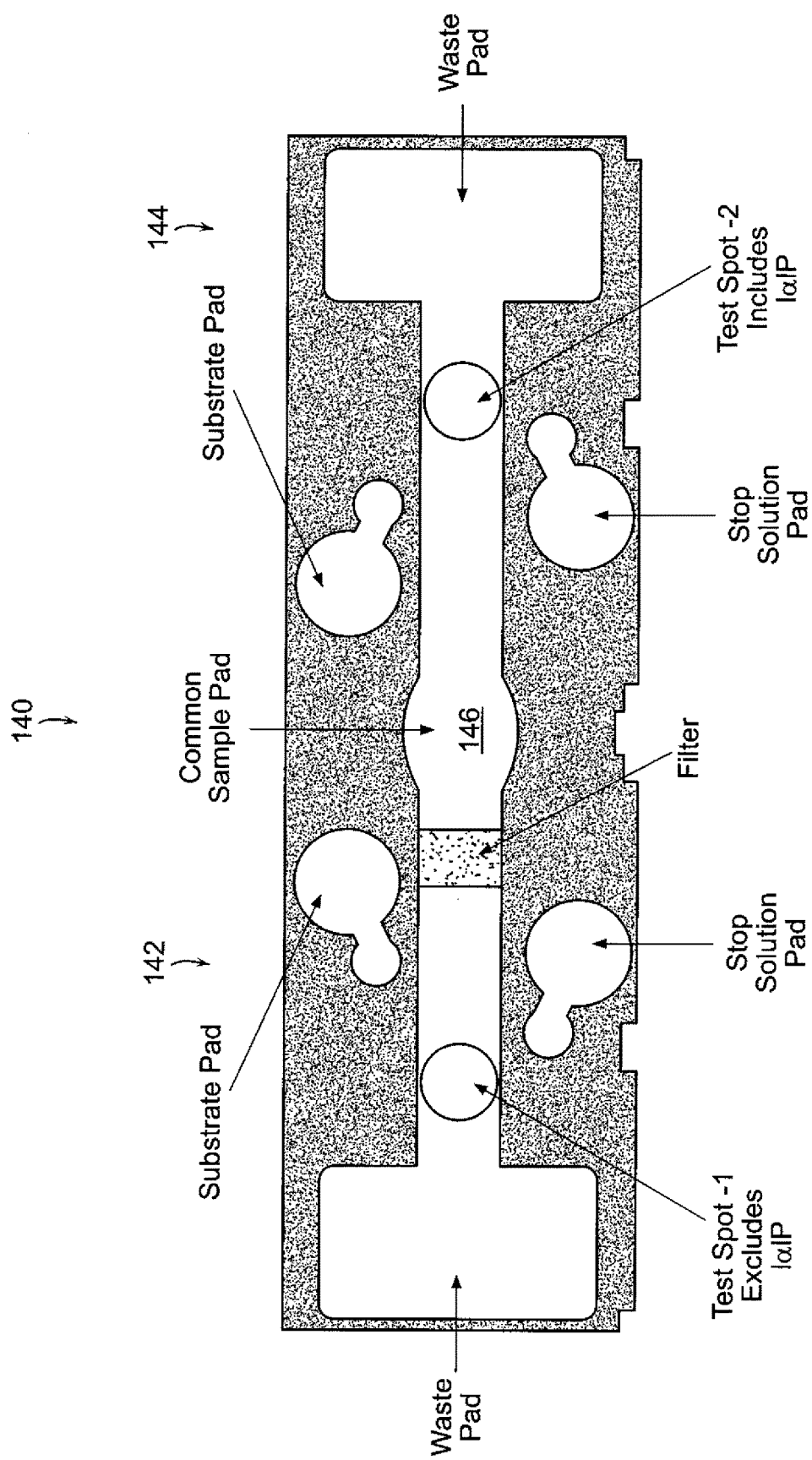
FIG. 12 shows an illustrative diagrammatic top view of a Dual Lab-on-Paper Device to detect the enzymatic activity when plasma is the sample solution.

The device on the right side of FIG. 12 will be identical to that of FIG. 11. The device 142 on the left may have a cut in the center channel to remove a portion of the paper and replaced it with a piece of nitrocellulose in which are immobilized monoclonal antibodies 69.26 (or 69.31). These are specific to IαIP and their function may be to remove IαIP from the plasma solution. As before, the substrate and stop solutions may be loaded in their respective pads and then the sample solution is loaded in the sample pad at which time the test begins. The sample fluid may split to the left and right devices and flow to the layers below to turn on the various valves. At the completion of the test, in the test spot-1, on the left, the intensity of the color will correspond to the action of all the other inhibitors on trypsin minus IαIP. In test spot-2 on the right the spot color intensity will correspond to all inhibitors including IαIP acting on the immobilized trypsin enzymes. The difference in intensities between the test spots will be a measure of the concentration of IαIP in the sample.

In certain embodiments therefore, the invention provides for the fabrication of fluid actuated diodes or valves in paper. Then, by combining the technology of test strips, the new 3D micro patterned valve techniques may be employed to provide multi-reagent paper-based microfluidic lateral flow devices, yielding highly flexible platforms that may meet the need for a sensitive, accurate, easy to use and low cost Lab-on-paper technology for the detection of biomarkers for near patient care and at the point-of-care.

Figure 13A:
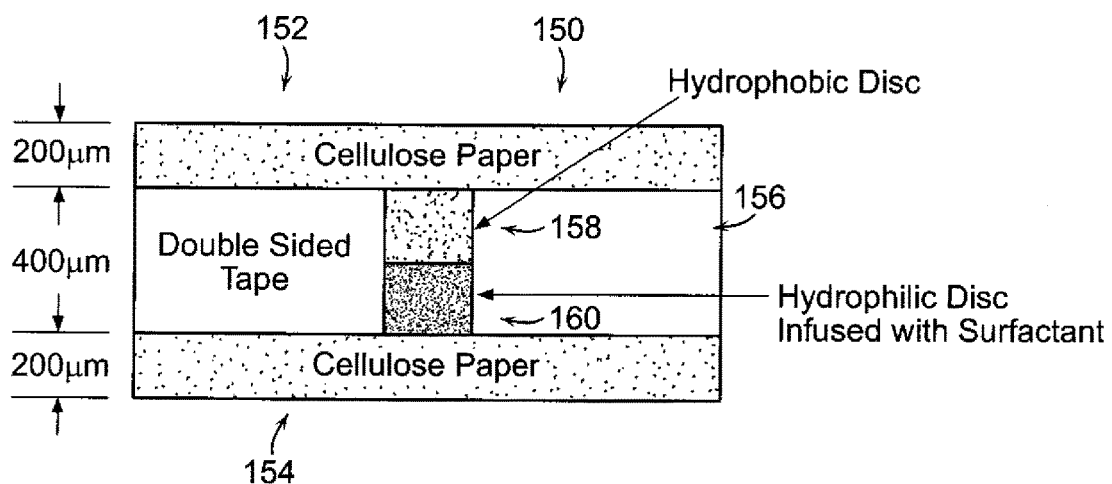
FIG. 13A shows an illustrative diagrammatic view of simplified structure of a 3D valve.
Figure 13B:
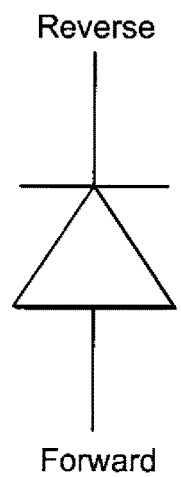
FIG. 13B shows an illustrative diagrammatic view of a valve symbol.

A diagrammatic cross sectional view of a 3D valve is shown at 150 in FIG. 13A and its corresponding symbol is shown diagrammatically in FIG. 13B. Similar to an electrical diode, the valve allows fluid to wick through it if it approaches from the forward direction but prevents any fluid to flow through it if it approaches from the reverse direction. However, unlike an electrical diode, once fluid has wicked through the valve, the valve is bridged and fluid may now flow in either direction. The valve 150 requires two sheets of paper 152, 154 held together by a sheet of double sided tape 156. In the tape is punched a hole and in that hole are inserted two discs. Both discs are made of paper. One disc, 158, is treated with allyltrichlorosilane which renders its fibers hydrophobic but it remains porous. The other disc, 160, consists of cellulose paper, and is infused with Tween 20 surfactant.

Figure 14A:
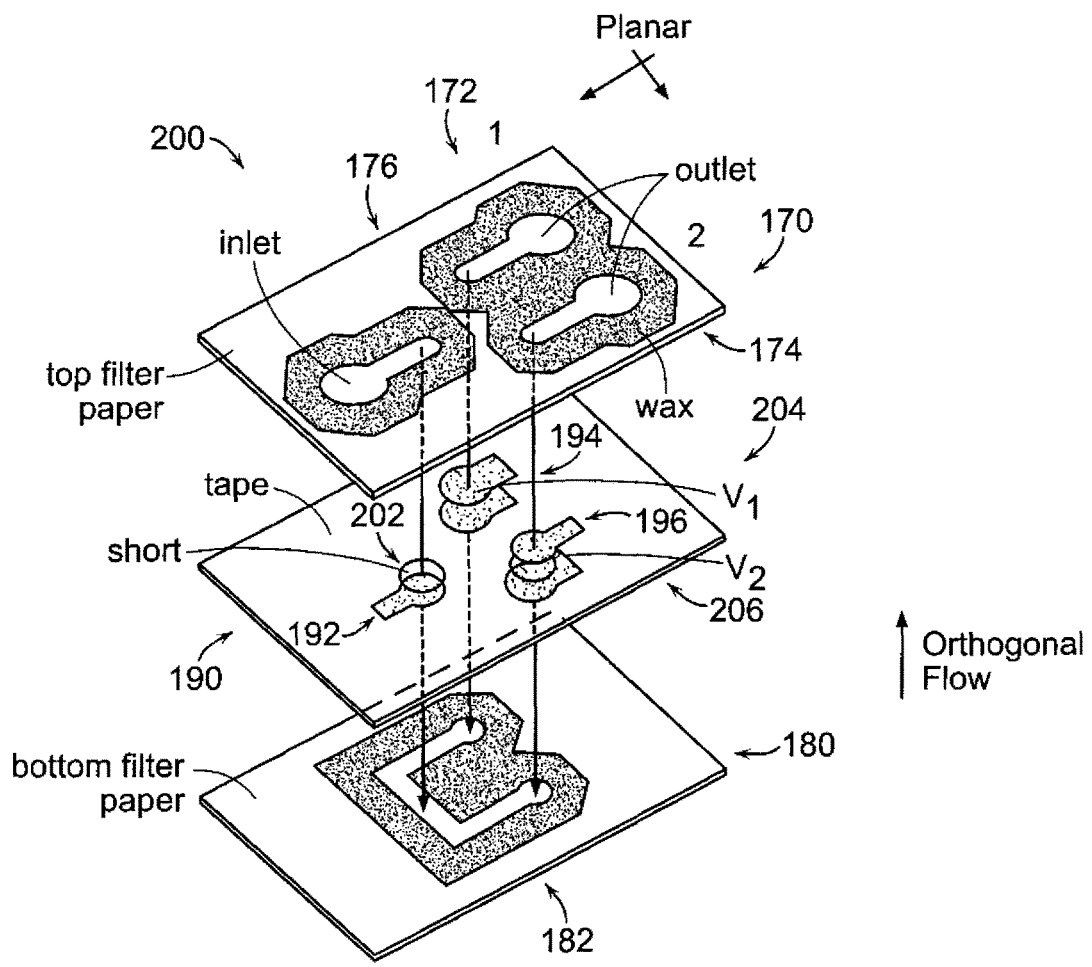
FIG. 14A shows an illustrative diagrammatic exploded view of a chip containing two 3D valves configured opposite to each other.
Figure 14B:
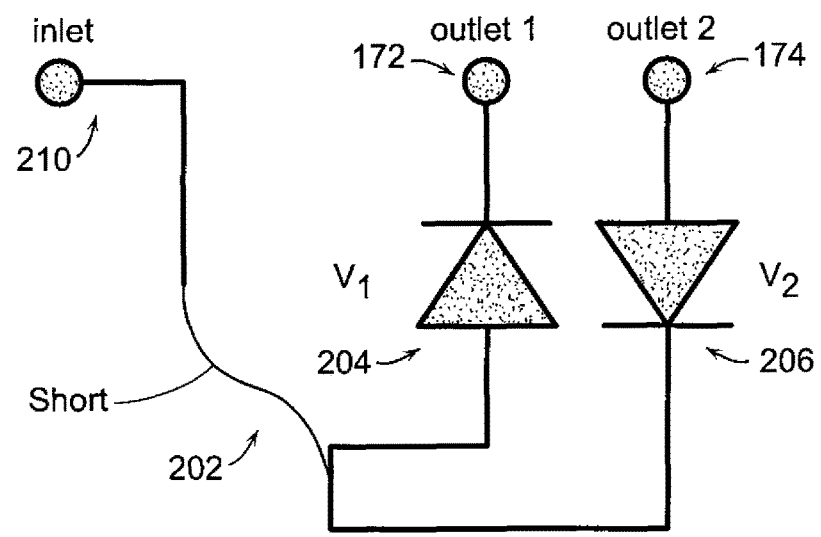
FIG. 14B shows an equivalent circuit representation of the chip containing two 3D configured valves opposite to each other as shown in FIG. 14A.

To demonstrate functionality of the 3D valves, a chip was fabricated containing two diodes each facing opposite to each other. An exploded view of the device is shown in FIG. 14A and its equivalent circuit diagram is shown in FIG. 14B. In FIG. 14A, in the top sheet of paper 170 are formed three hydrophilic channels 172, 174, 176 by enclosing virgin paper in hydrophobic wax walls. These walls are shown in black. In the bottom sheet 180, a U shaped pattern 182 is formed. The hydrophilic channels 172, 174, 176 surrounded by hydrophobic walls have been formed by the deposition of wax using a digital printer. The wax is subsequently melted into the paper to form solid (non-porous) hydrophobic walls.

Figure 15A:
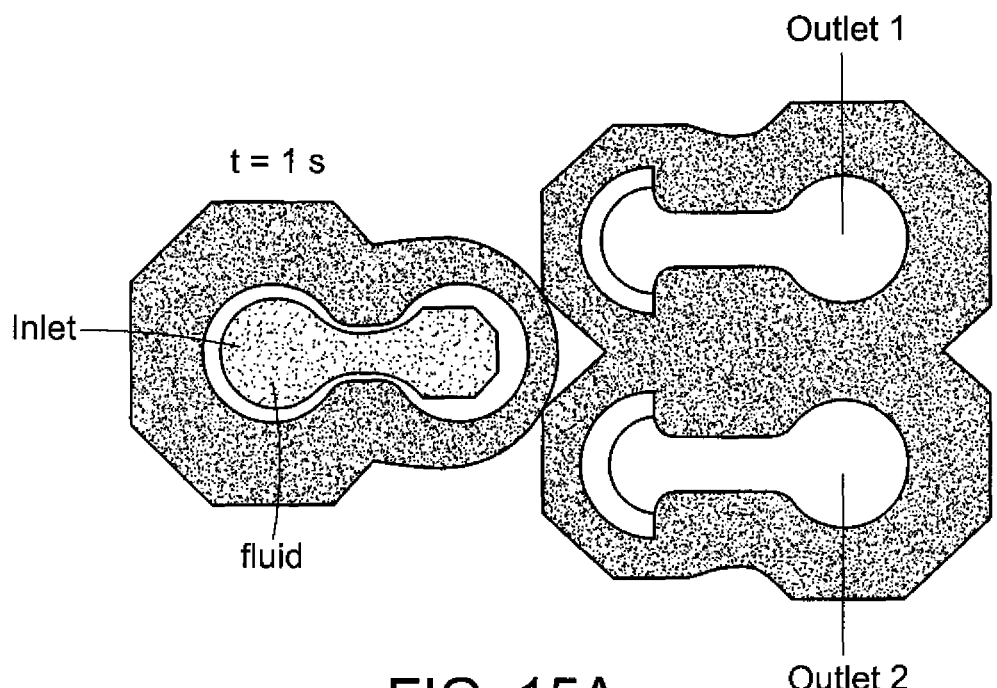
FIGS. 15A and 15B show illustrative diagrammatic views of a device in accordance with an embodiment of the invention at two stages of operation.
Figure 15B:
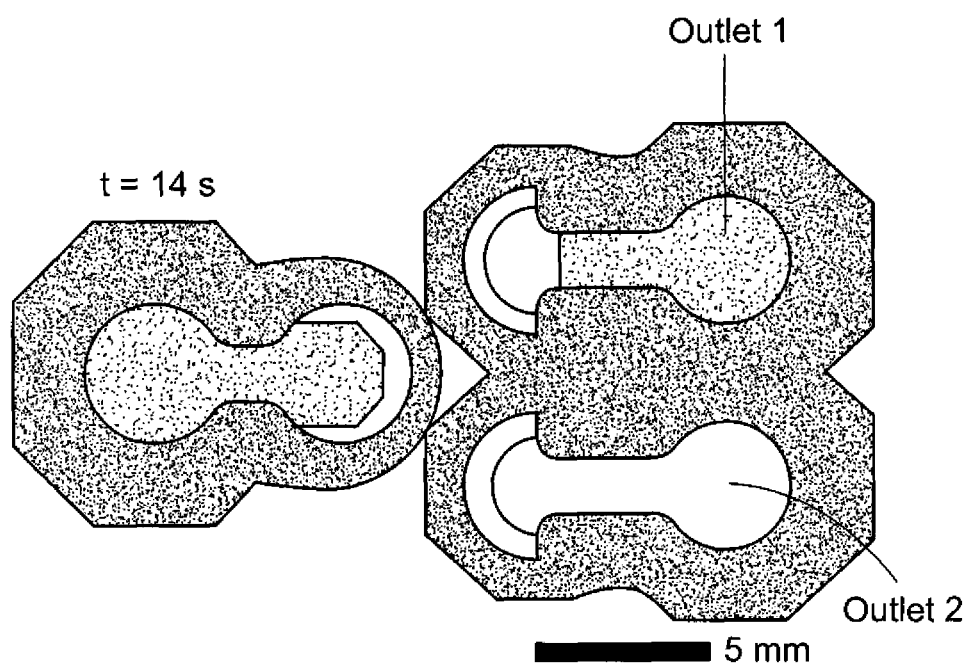
Figure 17A:
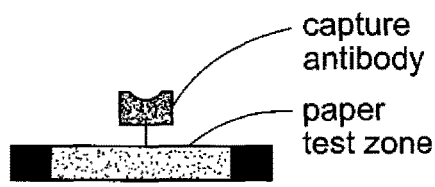
FIGS. 17A-17E show illustrative schematic views of different stages of the operation of a device in accordance with an embodiment of the invention.
Figure 17B:
Figure 17C:
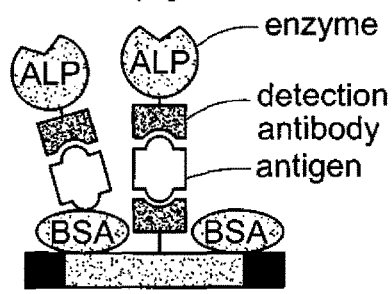
Figure 17D:
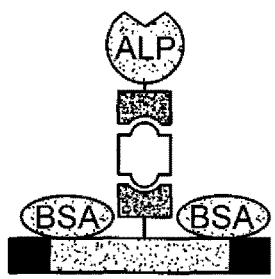
Figure 17E:
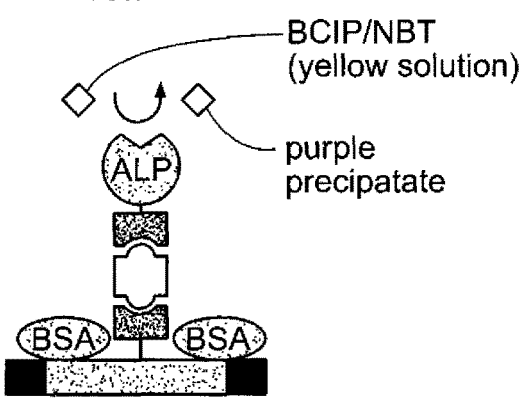

The middle sheet 190 is the double sided tape and there are three holes punched in it. The hole in the front left (192) is covered with a disc of pure cellulose paper. Its purpose is to form a fluidic short between the top layer and the bottom one. In the left-center hole 194, a surfactant disc is placed first and a hydrophobic disc is placed on top of it forming a diode pointing upward. In the center-right hole 196, the hydrophobic disc is placed first and the surfactant disc is placed on top of it forming a diode pointing downward. When a drop of fluid is loaded in the inlet pad 200, it first flows laterally and then downward to the paper layer below via the short 202. In the bottom layer the fluid splits into the two legs of the U pattern channel. The end of the left leg of the channel is connected to a diode 204 (V1) facing upward (Forward direction) thus the fluid can wick though it back up to the top layer of paper and appear on outlet 1. The other leg of the U is connected to a diode 206 (V2) that is facing downward (Reverse direction) which stops the fluid from wicking through it. Thus no fluid appears on outlet 2. This is shown graphically in the microphotographs of FIGS. 15A and 15B, where it is shown that the time for the fluid to flow from the inlet to outlet 1 is about 14 s. FIG. 14B shows an equivalent circuit diagram for the device of FIG. 14A.

Using valves described above, fluidic circuits may be built that allow for the triggering of one fluid flow by another. Such circuits may accept more than one fluid and perform an assay autonomously, that is without any operator intervention beyond applying the sample to the input pad. An ELISA test was conducted to detect Rabbit IgG in buffer. Paper based devices that can conduct ELISA are known, and these devices, generally require an operator or a robot to pipette the various reagents in sequence at specific times.

An exploded 3D view of a device in accordance with a further embodiment of the invention is shown in FIG. 16A, and a top view is shown in FIG. 16B. The device 210 includes a filter paper 212, a test membrane 214, a conjugate pad 216, a double-sided tape layer 218, another filter paper layer 220, another double-sided tape layer 222 and a blotting paper layer 224. In this device, the center channel width is 5 mm and the discs that formed each valve were 3 mm in diameter. In the top layer the center portion is similar to commercial LFTs. It consists of a main channel onto which the conjugate pad 216 is attached and further down is located the nitrocellulose membrane where the test spot is located. For simplicity, this experimental device does not have a control spot. After device fabrication, detection antibodies, monoclonal mouse anti-rabbit IgG tagged with the enzyme alkaline phosphatase, were deposited and dried at the conjugate pad. And at a spot in the nitrocellulose membrane were immobilized also monoclonal mouse anti-rabbit IgG as the capture antibodies.

To conduct the assay, first the wash fluid consisting of Superblocker blocking buffer and the substrate, which in this experiment is BCIP/NBT, were loaded into their respective inlet pads marked in the figure as wash and substrate inlets. Since there is a valve pointing upward beneath each of these pads, the fluids are blocked from wicking and simply remain there.

The sample fluid is subsequently loaded onto the sample pad 230. This fluid then splits into two portions. One portion flows along the center channel, first picking up the detection antibodies from the conjugate pad allowing for the formation of the rabbit IgG/mouse anti-rabbit IgG conjugate, then reaching the immobilized mouse anti-rabbit IgG antibodies where the sandwich assay is formed and is immobilized. A second portion of the sample fluid flows down to the second layer of paper 220 and along the channel there, where it triggers the valves to open and allows the wicking of the wash into the central channel where it helps remove unattached antibodies tagged with the enzyme. The wash fluid and sample fluid after they have gone by the nitrocellulose membrane again split into two paths. One path leads to the waste pad and another down the second layer of paper 220 where they reach the valves that have prevented the flow of the substrate solution. At this time the valves are turned on and the substrate begins to flow reaching the test area in the nitrocellulose membrane where it reacts with the immobilized enzymes and produces a color product whose density can be viewed and measured. A schematic of this ELISA protocol at the test spot as a function of time is shown in FIGS. 17A-17E.

FIG. 18A shows a dose response curve for an ELISA assay for Rabbit IgG. In FIG. 18B are photomicrographs of two devices at the completion of the test for two different concentrations of IgG showing that the test spot for 1 µg/mL is darker than the one for 0.1 µg/mL The dose response curve obtained for IgG concentrations ranging from 0 to 10 µg/mL is shown in FIG. 18A. The limit of detection in these experiments was 4.7 ng/mL and limit of quantification was 22.3 ng/mL. For these devices the sample volume needed was 130 µL, the wash was 60 µL and the substrate was 80 µL and the time to results was ~12 min.

Those skilled in the art will appreciate that numerous modifications and variations may be made to the above disclosed embodiments without departing from the spirit and scope of the present invention.

What is claimed is:

1. A micro-fluidic device comprising at least two paper flow path layers providing fluid flow in substantially parallel planar directions, and at least two fluid actuated valves positioned between the at least two paper flow path layers, said at least two fluid actuated valves for providing autonomous flow, said at least two fluid actuated valves are commonly coupled to a flow path, wherein said at least two fluid actuated valves comprise a first set of opposing valves with a first fluidic channel between them coupled to one of said two paper flow path layers while a second set of opposing valves are coupled to said first set of two opposing valves with a second fluidic channel between coupled to another of said two paper flow path layers for providing said autonomous flow, the first fluidic channel being coupled to said second fluidic channel at a common point on a third fluidic channel.

2. The micro-fluidic device as claimed in claim 1, wherein said fluid actuated valves are provided in an intermediate layer that is intermediate the at least two device paper layers.

3. The micro-fluidic device as claimed in claim 2, wherein said intermediate layer is formed of hydrophobic double sided tape, punched with a hole for each valve.

4. The micro-fluidic device as claimed in claim 1, wherein said micro-fluidic device includes a wash flow path.

5. The micro-fluidic device as claimed in claim 1, wherein each said fluid actuated valve is formed of a hydrophobic material adjacent a hydrophilic material.

6. A micro-fluidic device comprising at least two paper flow path layers providing fluid flow in substantially parallel planar directions, and at least two fluid actuated valves provided in an intermediate layer that are positioned between the at least two paper flow path layers, said at least two fluid actuated valves for providing autonomous flow, said at least two fluid actuated valves are oppositely positioned with respect to one another, wherein said at least two fluid actuated valves comprise a first set of opposing valves with a first fluidic channel between them coupled to one of said two paper flow path layers while a second set of opposing valves coupled to said first set of opposing valves with a second fluidic channel between coupled to another of said two paper flow path layers for providing said autonomous flow, the first fluidic channel being coupled to said second fluidic channel at a common point on a third fluidic channel.

7. The micro-fluidic device as claimed in claim 6, wherein said intermediate layer is formed of hydrophobic double sided tape, punched with a hole for each valve.

8. The micro-fluidic device as claimed in claim 6, wherein said micro-fluidic device includes a wash flow path.

9. The micro-fluidic device as claimed in claim 6, wherein each said fluid actuated valve is formed of a hydrophobic material adjacent a hydrophilic material.

\* \* \* \* \*

UNITED STATES PATENT AND TRADEMARK OFFICE
CERTIFICATE OF CORRECTION

| | |
|---|---|
| PATENT NO. | : 9,687,846 B2 |
| APPLICATION NO. | : 14/216503 |
| DATED | : June 27, 2017 |
| INVENTOR(S) | : Faghri et al. |

It is certified that error appears in the above-identified patent and that said Letters Patent is hereby corrected as shown below:

In the Specification

On Column 3, Line 24, "FIG. 1 A" should be "FIG. 1A".

Signed and Sealed this
Eighth Day of August, 2017

Joseph Matal
*Performing the Functions and Duties of the*
*Under Secretary of Commerce for Intellectual Property and*
*Director of the United States Patent and Trademark Office*